United States Patent [19]

Jacobsen et al.

[11] Patent Number: 4,863,715

[45] Date of Patent: Sep. 5, 1989

[54] METHOD OF NMR IMAGING USING A CONTRAST AGENT COMPRISING PARTICLES OF A FERROMAGNETIC MATERIAL

[75] Inventors: Trond Jacobsen; Jo Klaveness, both of Oslo, Norway

[73] Assignee: Nycomed AS, Oslo, Norway

[21] Appl. No.: 800,138

[22] PCT Filed: Mar. 28, 1985

[86] PCT No.: PCT/NO85/00017

§ 371 Date: Oct. 31, 1985

§ 102(e) Date: Oct. 31, 1985

[87] PCT Pub. No.: WO85/04330

PCT Pub. Date: Oct. 10, 1985

[30] Foreign Application Priority Data

Mar. 29, 1984 [GB] United Kingdom ............... 8408127

[51] Int. Cl.$^4$ .................... A61K 49/00; A61B 5/05; A61B 6/00
[52] U.S. Cl. ........................................ 424/9; 128/653; 128/654; 436/173; 436/806
[58] Field of Search ............... 424/4, 9, 1.1; 128/653, 128/654

[56] References Cited

U.S. PATENT DOCUMENTS

| 4,247,406 | 1/1981 | Widder et al. | 424/1.1 |
| 4,331,654 | 5/1982 | Morris | 424/38 |
| 4,675,173 | 6/1987 | Widder | 424/9 |
| 4,731,239 | 3/1988 | Gordon | 424/9 |
| 4,770,183 | 9/1988 | Groman et al. | 424/9 |

FOREIGN PATENT DOCUMENTS

| PCT/SE78/00001 | 6/1978 | PCT Int'l Appl. . |
| PCT/SE82/0381 | 11/1982 | PCT Int'l Appl. . |
| PCT/SE83/0106 | 3/1983 | PCT Int'l Appl. . |
| PCT/NO83/00014 | 4/1983 | PCT Int'l Appl. . |
| PCT/US84/00020 | 1/1984 | PCT Int'l Appl. . |
| 1174366 | 4/1968 | United Kingdom . |
| 1339537 | 12/1969 | United Kingdom . |

OTHER PUBLICATIONS

Runge, et al., Radiology, vol. 147, No. 3, (1983), pp. 789–791.

140Cl D85:3 B97879 60.OKU X10.OK 500 nm Merck, 1985, p. 269, Polyamid.

Drugs Effective in Iron-Deficiency and Other Hypochromic Anemias, Chap. 63, (Goodman & Gilman) p. 1316.

Magneto-Medicine: Biological Aspects of Ferromagnetic Fine Particles, Nakamura et al., "J. Applied Physics," vol. 42, #4, 3/-, pp. 1321–1324.

A Survey of Ferromagnetic Liquid Applications, M. Perry, pp. 219–230.

Magnetic Fluids in the Blood, Newbower, IEEE, vol. Mag 9; No. 3, Sep. 1973.

Hepatic Lipid Peroxidation In Vivo in Rats with Chronic Iron Overload, Bacon et al., J. Clin. Invest., vol. 71, Mar. 1983, pp. 429–439.

Primary Examiner—Robert J. Warden
Assistant Examiner—Stephen C. Wieder
Attorney, Agent, or Firm—Bacon & Thomas

[57] ABSTRACT

Ferromagnetic particles, conveniently embedded in or coated by a biotolerable polymer and held in dispersion in a physiologically acceptable dispersion medium, may be used as contrast agents in nmr imaging for the production of images suitable for use in diagnosis. Unlike paramagnetic nmr contrast agents, ferromagnetic nmr contrast agents give particularly good contrast in the $T_2$ dependent images.

36 Claims, 1 Drawing Sheet

METHOD OF NMR IMAGING USING A CONTRAST AGENT COMPRISING PARTICLES OF A FERROMAGNETIC MATERIAL

This invention relates to a method of nuclear magnetic resonance (nmr) imaging involving the use of ferromagnetic particles as contrast agents and to compositions comprising ferromagnetic particles suitable for such use.

Nmr has found increasing use since the early 1970's as a medical diagnostic tool, in particular as an imaging technique. The technique provides high resolution and differentiation of soft tissue without the use of potentially harmful radiation. For several years radiologists believed that, with the high contrast achieved in nmr imaging in soft tissues without the use of contrast agents, the use of contrast agents would not be necessary.

However, it has recently been found that paramagnetic complexes can be used with advantage to achieve enhanced contrast in nmr imaging so extending the diagnostic utility of the technique.

The nuclei of many atoms have a property called spin which is associated with a small magnetic moment. In the absence of an external magnetic field the distribution of the orientations of the magnetic moments is random. In the presence of a static magnetic field the nuclear magnetic moments precess about the field direction and there will be a net alignment in the field As R. S. First describes in "Nmr in medicine in the 1980's" (1983), in nmr imaging a patient is placed in a static field and a short radio frequency pulse is applied via a coil surrounding the patient. The radio frequency or RF signal is selected for the specific nuclei (e.g. $^1H$, $^{19}F$) which are to be resonated. The RF pulse causes the magnetic moments of the nuclei to align with the new field and to precess in phase, and on termination of the pulse the moments return to the original distribution of alignments with respect to the static field and to a random distribution of precession phases giving off a nuclear magnetic resonance signal which can be picked up by a receiving coil. The nmr signal is generally from $^1H$ nuclei and represents a proton density map of the tissue being studied.

Two additional values can be determined when the RF pulse is turned off and the nuclear magnetic moments are relaxing or returning to equilibrium orientations and phases. These are $T_1$ and $T_2$, the spin-lattice and spin-spin relaxation times. $T_1$ represents a time characteristic of the return to equilibrium spin distribution, i.e. equilibrium alignment of the nuclear magnetic moments in the static field. $T_2$ on the other hand represents a time characteristic of the return to random precession phase distribution of the nuclear magnetic moments.

The nmr signal that is generated thus contains information on proton density, $T_1$ and $T_2$ and the images that are generated are generally the result of complex computer data reconstruction on the basis of that information.

The potential application of contrast agents in extending the diagnostic utility of nmr imaging is discussed by R. C. Brasch in Radiology 147 (1983) 781. Although numerous methods of contrast are available, many, such as manipulation of tissue temperature, viscosity or hydration, are clearly not clinically feasible and the most advantageous prior art technique appears to be the use of paramagnetic contrast agents to reduce the spin-lattice relaxation time $T_1$.

A paramagnetic substance is one which contains one or more fundamental particles (electrons, protons or neutrons) with a spin whose effect is not cancelled out by another particle with like spin. These particles create a small magnetic field which can interact with neighbouring nuclear magnetic dipoles to cause a reorientation of the dipole, i.e. a change in nuclear spin and precession phase.

Since the magnetic field created by an electron is much greater than that created by a proton or a neutron, in practice only ions, molecules, radicals or complexes which are paramagnetic through containing one or more unpaired electrons are used as paramagnetic nmr contrast agents.

The contrast effect of paramagnetic ions and complexes is predominantly the result of reduction in $T_1$ (cf. German Offenlegungsschrift No. 3129906). However, as discussed by R C Brasch in Radiology 147 (1983) 781, paramagnetic stable free radicals will also cause some reduction in $T_2$. Nevertheless the relative reduction of $T_1$ is greater than that of $T_2$.

The use of paramagnetic contrast agents in nmr imaging has been extensively investigated and solutions and colloidal dispersions of such agents have been proposed for oral and parenteral administration in conjunction with diagnostic imaging.

As yet, however, there have been no nmr contrast agents available for use in nmr imaging which are capable of selectively enhancing contrast between different tissue types in the $T_2$ image.

We have now surprisingly found that ferromagnetic particle dispersions can be used as contrast agents in nmr imaging, contrast being achieved by significant reduction in $T_2$ (accompanied by a generally lower relative reduction in $T_1$).

Ferromagnetic particles contain atoms which within volumes called domains have their magnetic moments (resulting from their unpaired electrons) aligned. Ferromagnetism is thus a cooperative phenomenon unlike paramagnetism and can only exist in aggregations of atoms i.e. particles.

Ferromagnetic particles are capable of being magnetised, that is a particle containing a large number of atoms may generate a net magnetic field even in the absence of an external field. In paramagnetic particles having large numbers of atoms on the other hand, the magnetic dipoles of the individual paramagnetic atoms or molecules will randomise in the absence of an external field and thus no net field would be generated.

This ability to become magnetised and generate a relatively strong magnetic field is a major reason why the use of ferromagnetic particles as contrast agents in nmr imaging could have been considered to be contraindicated, especially in in vivo diagnostic imaging.

Thus in nmr spectroscopy, from which technical field nmr imaging has developed, the presence of ferromagnetic particles is a well-known source of inaccuracy and it is not unusual to use a magnet to remove tiny ferromagnetic particles from samples to avoid the reduction in measured spectrum resolution and accuracy that results from the presence within the sample of the local field inhomogeneities that the particles cause.

Similarly, if the ferromagnetic particles become magnetised then they may be expected to cluster. Thus while paramagnetic contrast agents can achieve substantially uniform distribution of the paramagnetic centres whether in solution or in colloidal dispersion, it might be thought likely that a dispersion of ferromagnetic particles might cluster and so not distribute uniformly. In the case of parenterally administered dispersions, the occurrence of such clustering would have been considered dangerous to the patient and the use of ferromagnetic particles thus not considered suitable.

Furthermore, the strength of the field generated by a ferromagnetic particle is so much greater than that generated by paramagnetic particles that it would have been expected that the contrast effect produced in an nmr image by the presence of ferromagnetic particles in the sample under investigation would extend over such a distance as to be likely to blur the boundary on the image between tissue containing ferromagnetic particles and tissue not containing such particles, e.g. the walls of blood vessels or of the gastrointentinal tract for iv and orally administered particles respectively.

P. Mansfield and P. G. Morris in "Advances in Magnetic Resonance - Supplement 2" Ed. J. S. Waugh (1982) page 324, Academic Press N.Y. have suggested the oral administration of colloidal particles of pure iron in the form of an iron meal so that its progress could be tracked by the strong localised inhomogeneity produced. However, there is no indication as to whether $T_1$ or $T_2$ should be determined and no suggestion that the iron particles should impregnate tissues as compared with remaining as a plug of ferromagnetic material passing through the alimentary system.

Orally administrable particulate ferromagnetic compositions are also proposed in Brit. Pat. No. 1339537, althoug their suggested use is as X-ray contrast agents in place of conventional barium meals.

The use of certain ferromagnetic polymer particles for therapeutic and diagnostic purposes is suggested broadly in International Pat. Application Publication No. WO 8303920 which describes the preparation of monodisperse ferromagnetic polymer particles. This publication refers to the use of such particles in (in vitro) cell separation whereby separation by centrifugation may be replaced by the much simpler method of magnetic extraction. It is also suggested that such particles may be used as carriers for pharmaceuticals which can then be transported to the desired location using a magnetic field.

R. S. Newbower (IEEE Transactions on magnetics Mag 9 (1973) 447) and M. P. Perry (Proceedings Int. Adv. Course Workshop (1977)) have described therapeutic and diagnostic applications in which a stable colloidal dispersion of ferromagnetic particles is introduced into the bloodstream. The particles can be guided magnetically to a vascular malfunction, e.g. a cerebral aneurysm, and may be held there by a magnetic field to seal the defect. Alternatively by disposing a permanent magnet about an artery a plug of ferromagnetic particles can be caused to form which halts blood flow in the artery; this may be beneficial during surgery where the artery could be damaged if sealed by clamping. A further use of the injected dispersion is for blood flow tracing as the dispersion can be detected by its magnetic susceptibility alone.

There has however been no suggestion in the prior art that ferromagnetic particles could be used as $T_2$ contrast agents in nmr imaging.

In one aspect, the present invention provides a method of nmr imaging Of a sample wherein a contrast agent is introduced into said sample and an image of said sample is generated, characterized in that said contrast agent comprises a plurality of ferromagnetic particles, conveniently in the form of a dispersion of such particles, and in that said image is a $T_2$ dependent image, preferably a $T_2$ image.

In the method of the invention the $T_2$-reducing contrast effect of the ferromagnetic particles is of particular interest and while nmr imaging may be used to generate separate intensity, $T_2$ and $T_l$ images, a considerable saving in required computing time and capacity may be achieved by producing the $T_2$ image alone or the $T_2$ and either the $T_l$ or the intensity image.

In the method of the present invention, the relative magnitude of the contrast effect will be dependent on several sample-unrelated factors such as the particle density, the particle ferromagnetic content and the mean particle size. As a general rule the reduction in both $T_1$ and $T_2$ achieved by use of the contrast agent will increase with these factors. However, the relative reduction of $T_2$ and $T_1$ may be particularly sensitive to ferromagnetic content and particle size with increasing ferromagnetic content causing a relatively higher reduction in $T_2$ and with the relative reduction in $T_2$ being smaller as particle size decreases.

The mean ferromagnetic particle size will conveniently be less than 50 $\mu$m, preferably 0.002 to 50 $\mu$m and advantageously from about 0.1 to 20$\mu$. For parenteral administration mean ferromagnetic particle size will preferably be in the range of 0.1 to 10$\mu$ while for administration directly into the digestive tract (e.g. orally) or into the bladder, the uterus, the biliary duct or the parotid duct, the particularly preferred range will be 5 to 20 $\mu$m. The ferromagnetic content of the particles will suitably be from 0.1 to 100%, preferably from 0.5 to 50%, by weight.

The ferromagnetic particles may be of any ferromagnetic material, such as pure iron or magnetic iron oxides such as magnetite, $\gamma Fe_2O_3$, manganese, cobalt or nickel ferrites and may if desired have non-ferromagnetic coatings or matrices, e.g. polymer coatings, for example to avoid chemical reaction between the sample and the particles or to aid dispersion. Where it is desired to use particles having a polymer coating or matrix within which the ferromagnetic material is distributed, the particles are preferably prepared according to the method of J. Ugelstad et al. (see for example International Patent Application Publication No. WO 83/03920). To be suitable for routine in vivo imaging, the particles should not be radioactive.

Nmr imaging is particularly valuable as a diagnostic tool as it makes it possible to image tissue and organs in vivo. Different organs and different tissues, e.g. cancerous and normal tissues within the same organ, exhibit different characteristic proton intensities and $T_1$ and $T_2$ relaxation times. Thus ferromagnetic contrast agents are particularly useful in nmr imaging diagnosis.

In a preferred aspect, the method of the invention is a method of nmr imaging of a human or non-human animal body (or of tissue extracted therefrom) in which method the nmr contrast agent, conveniently in the form of a dispersion, is introduced into the region to be imaged and $T_2$ dependent images, preferably $T_2$ images, suitable for use in diagnosis are generated of body tissue or sites.

The administration of the ferromagnetic contrast agent may be parenteral, suitably achieved by injection (e.g. i.v.), oral (e.g. by ingestion), rectal or by introduction through a catheter into the bladder uterus, biliary duct or parotid duct. However, administration to body sites from which the contrast agent may be discharged from the body without passing through body tissue, e.g. administration to the gut, the bladder, the uterus etc, is preferred. Where the organs to be imaged are the liver, spleen, bone marrow etc. i.v. administration will be preferred. It has been found in animal experiments that elimination of iv administered ferromagnetic particles from the blood is extremely rapid.

The ferromagnetic particles may comprise free ferromagnetic particles or ferromagnetic material embedded in or coated with a non-ferromagnetic matrix or coating. For parenteral administration the coating or matrix material is preferably a biodegradable polymer while for administration directly into the digestive tract or into the bladder, uterus etc., the material is preferably a biotolerable polymer and especially preferably a non-biodegradable polymer, e.g. a cellulose derivative.

In a further aspect, the invention provides an nmr contrast agent for administration to the human or non-human animal body to serve as a contrast agent in the generation of $T_2$ dependent images, preferably $T_2$ images, said nmr contrast agent comprising a dispersion of ferromagnetic particles in a physiologically acceptable dispersion medium.

In a still further aspect, the invention provides the use of ferromagnetic particles for the manufacture of an nmr contrast agent for use in a method of diagnosis practised on the human or non-human animal body which method includes generation of a $T_2$ dependent image, preferably a $T_2$ image, and diagnosis using said image.

In another aspect, the invention provides a package comprising the nmr contrast agent of the invention in a container therefor together with instructions for the use thereof in a method of nmr imaging.

The contrast agent of the invention, if for parenteral administration, is advantageously a dispersion in a sterile physiologically acceptable medium, e.g. isotonic aqueous solutions which may contain surfactants such as for example polysorbate 80. For parenteral administration the ferromagnetic particles are preferably embedded in or coated by a biodegradable polymer whose degradation products are physiologically acceptable.

The contrast agent of the invention, if for administration directly to the digestive tract (e.g. orally) or to the bladder, uterus etc, is advantageously dispersed in a physiologically acceptable medium, e.g. aqueous solutions containing surfactants and/or viscosity increasing substances such as for example cellulose derivatives.

Using such a viscosity enhancing agent, the contrast agent may be caused to coat the walls of the digestive tract and so make feasible contrast enhancement of images of the intestines. Using orally administered paramagnetic contrast agnts, contrast enhancement of the digestive tract is not readily achieved beyond the stomach.

Where the contrast agent is for administration directly into the digestive tract (e.g. orally) or into the bladder, uterus, etc, it is especially preferred that the ferromagnetic particles should be of about the same specific gravity as the surrounding fluid (gastro-intestinal fluid or urine) and particles having specific gravity of about 1.07 are preferred.

For administration into the digestive tract or the bladder the ferromagnetic particles are preferably embedded in or coated by a biotolerable polymer, i.e. a polymer which is physiologically acceptable and either non-biodegradable or biodegradable to yield degradation products which are physiologically acceptable. Non-biodegradable polymers are particularly preferred as the ferromagnetic material released by polymer degradation may be soluble in the gastrointestinal fluid or if very fine may be absorbed by the body. Dissolution of the ferromagnetic material may release paramagnetic ions thereby reducing the contrast effect in the proton intensity image as the $T_1$ reducing effect of paramagnetic material tends to increase the proton intensity whereas the $T_2$ reducing effect of ferromagnetic material tends to decrease the proton intensity (see hereinafter for the dependence of proton intensity I on $T_1$ and $T_2$).

Particularly suitably the contrast agents of the invention comprise ferromagnetic particles embedded in or coated by a polymer free from adsorbed or absorbed drugs. The ferromagnetic particle sizes and ferromagnetic contents are preferably within the ranges specified above.

The ferromagnetic particles in the nmr contrast agents of the invention are administered dispersed in a dispersion medium. Thus before administration uniform particle dispersion is preferably achieved by shaking and sonication. For simplicity, the term "dispersion" is used herein to relate to true dispersions, suspensions and colloids.

The concentrations of the ferromagnetic material in the contrast agent will be dependent on the administration form and on the particular organs or tissue to be studied. Advantageously the dosage should be sufficient to produce a concentration of about 0.1 mmol of the ferromagnetic metal (e.g. Fe) per kilogram of the organ to be studied at the organ in question. Generally total dosages will be in the range of $10^{-4}$ to $10^1$ mmol of the ferromagnetic metal (e.g. Fe) per kg bodyweight, preferably about $10^{-3}$ to $10^{-1}$ mmol/kg. The dispersions themselves conveniently contain about 0.1 to 10% by weight of ferromagnetic material as a whole.

The ferromagnetic particles in the parenterally administerable contrast agents of the invention are preferably substantially uniform in particle size to achieve uniform contrast in equivalent tissue areas. In general, particle diameters range from 0.002 to 50 $\mu$m and, for parenteral administration, a standard deviation in diameter of less than 10% is particularly preferred. For administration directly into the digestive tract particle size should not be so low as possibly to result in the particles being absorbed from the tract.

In diagnosis using nmr images, the nmr image or picture that is generated can be based upon the different $T_2$ values of neighbouring tissues. By reducing $T_2$ in a tissue, it will be possible to get a contrast enhancement.

The particulate form of the ferromagnetic material in the contrast agent makes it possible for the agent to be tissue-specific. Particularly suitable target organs for intravascularly administered particles are the liver and spleen due to the reticuloendothelial system. One possible application of parenterally administered particles may be to diagnose primary cancer and metastases in the liver.

The liver is the organ in the abdomen with the shortest relaxation times ($T_1$ and probably $T_2$ also). Generally, tumors have longer relaxation times ($T_1$ and $T_2$) than normal tissues. Forty percent of the liver cells are made up of reticuloendothelial cells. Intravenously injected particles are distributed macroscopically uniformly within a normal liver. In both hepatomas and metastases the capability to pick up particles is reduced or does not exist. Intravenously administered ferromagnetic particles may thus selectively reduce $T_2$ in normal liver tissue. $T_2$ in normal liver tissue is smaller than $T_2$ in liver cancer tissue and in surrounding tissues, and so further reduction of $T_2$ in the normal liver tissue by the use of ferromagnetic contrast agents will raise the contrast between normal liver tissue and cancer liver tissue making diagnosis simpler. The ability to diagnose metastases in the liver at an early stage is very important, because more than 30% of all cancer forms result in liver metastases, and often it is possible to diagnose the metastases in the liver before the primary tumor can be detected.

The effect of the use of ferromagnetic contrast agents in the diagnosis of liver cancers using nmr imaging is illustrated schematically in the accompanying drawings, in which.

Figure 1:
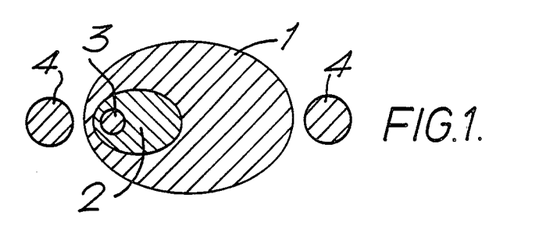
FIG. 1 is a schematic representation of a $T_2$ image of a transverse cross section of the body through a liver which contains a metastasis.
Figure 2:
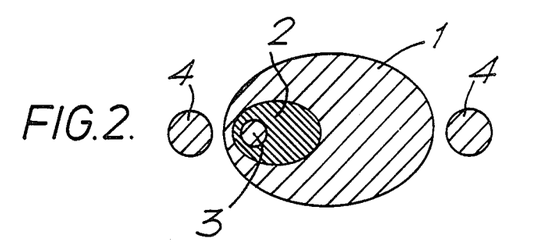
FIG. 2 is a schematic representation of a $T_2$ image of the cross section of FIG. 1 following introduction of a ferromagnetic contrast agent into the liver.

Referring to FIGS. 1 and 2, these show a cross section through the abdomen 1, arms 4 and liver 2. The liver is shown as containing a metastasis 3. The shading of the body areas corresponds to the local $T_2$ value with light shading indicating a $T_2$ of about 70 ms, medium shading about 40 ms and heavy shading about 10 ms.

Figure 3:
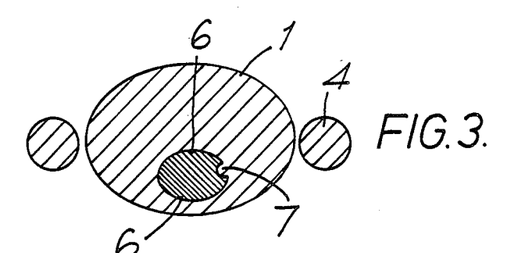
FIG. 3 is a schematic representation of a $T_2$ dependent image of a cross section of the body through the bladder after introduction of a ferromagnetic contrast agent into the bladder through a catheter.

Referring to FIG. 3, the ferromagnetic particle containing urine 5 enables the contour of the bladder wall 6 to be visualized and the presence of a tumour 7 to be detected.

Figure 4:
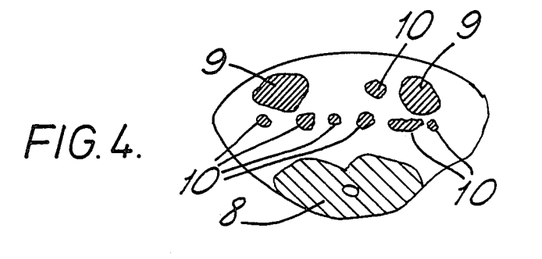
FIG. 4 is a schematic representation of the $T_2$ dependent image of a transverse cross-section of a rabbit abdomen.

Referring to FIG. 4, this shows a schematic representation of an nmr image produced on a scan through a rabbit abdomen using the spin-echo technique (repetition time 500 ms (TR), echo time 50 ms (TE)) after oral administration to the rabbit of 100 μmol Fe/kg of the suspension of Example 6 hereinafter. The scan enables the large intestines 9 and the small intestines 10 which contain the contrast agent to be differentiated clearly from muscle 8.

The contrast enhancement achieved with the ferromagnetic particles depends upon the pulse sequences and pulse parameters used in measuring the nmr image in question. In addition to the effect on the $T_2$ image, the ferromagnetic particles may image the proton intensity image. The proton intensity is a function of both $T_1$ and $T_2$:

$$I = Hf(v)\exp(-a/T_2)(1-\exp(-b/T_1))$$

Where H is the local hydrogen concentration, a and b are parameters of the nmr instrument and f(v) is a function of both the speed at which the hydrogen nuclei move through the region being imaged and the fraction of the total number of nuclei that are moving. Thus an increase in $T_1$ reduces the intensity while an increase of $T_2$ increases the intensity. A selective $T_2$ agent will thus alter the proton intensity.

The invention will now be further illustrated by the following non-limiting Examples:

EXAMPLES 1-6

Preparation of ferromaqnetic dispersions

Ferromagnetic polymer particles prepared according to the process of J. Ugelstad et al (WO 83/03920) and having the properties listed in Table I were used in the preparation of the contrast agents.

GENERAL PROCEDURE FOR EXAMPLES 1-3

The ferromagnetic particles were suspended in 8 ml sterile water (0.5% polysorbate 80). The suspension was sonicated and shaken for 30 minutes, centrifuged and the particles resuspended in a solution of bovine serum albumin (200 mg) in sterile water (8 ml). After shaking for 3 hours the suspension was centrifuged, the particles washed with 0.9% NaCl (0.1% polysorbate 80) (2 × 8 ml) and resuspended in the same suspension medium 10 ml.

EXAMPLE 1

|   |   |   |
|---|---|---|
|   | 57.7 mg | Particles (Type 1) (19.4% Fe) |
|   | 10 mg | Polysorbate 80 |
| ad | 10 ml | 0.9% aqueous NaCl solution |

EXAMPLE 2

|   |   |   |
|---|---|---|
|   | 1000 mg | Particles (Type 2) (30.2% Fe) |
|   | 20 mg | Polysorbate 80 |
| ad | 20 ml | 0.9% aqueous NaCl solution |

EXAMPLE 3

|   |   |   |
|---|---|---|
|   | 1000 mg | Particles (Type 3) (29.2% Fe) |
|   | 20 mg | Polysorbate 80 |
| ad | 20 ml | 0.9% aqueous NaCl solution |

GENERAL PROCEDURE FOR EXAMPLES 4 AND 5

The ferromagnetic particles were suspended in 0.9% NaCl (0.3% polysorbate 80) to 10ml. The suspensions were sonicated and shaken 10 minutes.

EXAMPLE 4

|   |   |   |
|---|---|---|
|   | 765 mg | Particles (Type 3) (29.2% Fe) |
|   | 30 mg | Polysorbate 80 |
| ad | 10 ml | 0.9% aqueous NaCl solution |

EXAMPLE 5

|   |   |   |
|---|---|---|
|   | 740 mg | Particles (Type 2) (30.2% Fe) |
|   | 30 mg | Polysorbate 80 |
| ad | 10 ml | 0.9% aqueous NaCl solution |

EXAMPLE 6

(Suspension for administration directly to the digestive tract or the bladder.)

Carboxymethylcellulose (92 mg) and polysorbate 80 (4 mg) were added to water (3.5 ml). The stirred mixture was warmed to 80° C.

After cooling, 1187 mg of particles (Type 3) were added and the suspension was homogenized by vigorous shaking and 15 minutes sonication.

TABLE I

| Particle Type | % Fe | μm diameter | Particle Surface |
|---|---|---|---|
| 1 | 19.4 | 3 | porous |
| 2 | 30.2 | 1.5 | porous |
| 3 | 29.2 | 3 | porous |
| 4 | 5.0 | 0.8 | hydrophilic |
| 5 | 2.0 | 0.8 | hydrophilic |
| 6 | 0.5 | 0.8 | hydrophilic |
| 7 | 0.5 | 0.8 | hydrophilic |
| 8 | 0.5 | 0.8 | hydrophilic |
| 9 | 32.9 | 1.5 | porous |
| 10 | 18.2 | 1.5 | porous |
| 11 | 9.4 | 1.5 | porous |
| 12 | 12.0 | 2.5 | hydrophilic |
| 13 | 30.0 | 3.0 | hydrophilic |
| 14 | 7.2 | 15.0 | PFA+ |
| 15 | 9.8* | 3.0 | porous |
| 16 | 6.8++ | 3.0 | porous |

*9.8% Fe, 4.3% Mn
++6.8% Fe, 1.7% Mn
+polyfurfuryl alcohol layer

EXPERIMENTAL RESULTS

Measurements of $T_1$ and $T_2$

Nmr measurements were performed for protons at a frequency of 10.7 MHz with pulse sequences: ($90°$- $\tau$- $90°$) and ($90°$- $\tau$- $180°$- $\tau$) for $T_1$ and $T_2$ respectively.

The temperature was 37° C.

The ferromagnetic suspensions were homogenized by sonication and vigorous shaking.

The in vitro experiments were performed in the following solutions:

| | | | |
|---|---|---|---|
| (1) | Distilled and ion-exchanged water | 68.76 | vol. % |
| | Glycerol | 31.75 | vol. % |
| (2) | Distilled and ion-exchanged water | 53 | weight % |
| | Glycerol | 31.4 | weight % |
| | Gelatin | 15.0 | weight % |
| (3) | Human plasma | | |
| (4) | Heparinized blood (rabbit) | 67.0 | vol. % |
| | Homogenized liver (rabbit) | 33.0 | vol. % |
| (5) | 1% Methylcellulose in water. | | |

The in vivo experiments were performed as follows: Particle suspensions were injected i.v. in rats and rabbits. Blood samples were taken at various points of time. The animals were killed and the relaxation times ($T_1$ and $T_2$) in both the blood samples and the various organs were measured.

In vitro measurements

The relaxation times ($T_1$ and $T_2$) have been measured in different samples with various ferromagnetic monodisperse polymer particles and with various commercially available ferromagnetic particles and are summarized in Tables II, III and IX below. The ferromagnetic material in the particles includes various magnetic iron oxides and other ferrites. The size of the particles varied from 0.01 μm to 100 μm and their ferromagnetic content from 0.5 to 100%.

TABLE II

| Example No. | Particle Type | Particle diameter (μm) | Amount of Fe in particle (%) | Concentration of Fe in sample (mmol/kg) |
|---|---|---|---|---|
| 7 | 4 | 0.8 | 5.0 | 0.1 |
| 8 | 4 | 0.8 | 5.0 | 0.2 |
| 9 | 5 | 0.8 | 2.0 | 0.1 |
| 10 | 5 | 0.8 | 2.0 | 0.2 |
| 11 | 6 | 0.8 | 0.5 | 0.1 |
| 12 | 7 | 0.8 | 0.5 | 0.1 |
| 13 | 8 | 0.8 | 0.5 | 0.1 |
| 14 | 9 | 1.5 | 32.9 | 0.1 |
| 15 | 2 | 1.5 | 30.2 | 0.1 |
| 16 | 10 | 1.5 | 18.2 | 0.1 |
| 17 | 11 | 1.5 | 9.4 | 0.1 |
| 18 | 12 | 2.5 | 12 | 0.1 |
| 19 | 13 | 3 | 30.0 | 0.1 |
| 20 | 3 | 3 | 29.2 | 0.1 |
| 21 | 1 | 3 | 19.4 | 0.1 |
| 22 | 14* | 15 | 4.7 | 0.1 |
| 23 | 16 | 0.8 | 0 | 0 |

| | SAMPLES | | | | | | | |
|---|---|---|---|---|---|---|---|---|
| | Distilled Water/ Glycerol | | Human Plasma | | Homogenized Liver and Blood | | Distilled Water/ Glycerol/ Gelatin | |
| Example No. | $T_1$ (ms) | $T_2$ (ms) | $T_1$ (ms) | $T_2$ (ms) | $T_1$ (ms) | $T_2$ (ms) | $T_1$ (ms) | $T_2$ (ms) |
| 7 | 1033 | 77 | 881 | 77 | 244 | 37 | | |
| 8 | | | | | 178 | 23 | | |
| 9 | 1054 | 128 | 942 | 92 | 407 | 56 | | |
| 10 | | | | | 318 | 38 | | |
| 11 | 602 | 50 | 481 | 42 | 187 | 30 | | |
| 12 | 651 | 56 | 499 | 55 | | | | |
| 13 | 774 | 69 | 573 | 68 | | | | |
| 14 | 1685 | 169 | 1646 | 180 | | | | |
| 15 | | | | | | | 812 | 46 |
| 16 | 1631 | 187 | 1507 | 139 | | | | |
| 17 | 1679 | 548 | 1727 | 387 | | | | |
| 18 | | | | | | | 835 | 60 |
| 19 | | | | | | | 866 | 49 |
| 20 | 1687 | 176 | 1618 | 173 | | | | |
| 21 | | | | | | | 870 | 60 |
| 22 | | | | | | | 680 | 182 |
| 23 | 1706 | 658 | 1693 | 325 | | | | |
| Control | 1710 | 800 | 1660 | 430 | 474 | 106 | 890 | 300 |

*Polyfurfuryl alcohol layer

TABLE III

| Example No. | Particle Type | % Fe | % Mn | [Fe] mmol/kg | [Mn] mmol/kg |
|---|---|---|---|---|---|
| 24 | 15 | 9.8 | 4.3 | 0.1 | 0.045 |
| 25 | 16 | 6.8 | 1.7 | 0.1 | 0.025 |
| 26 | Magnetite* | 72.4 | 0 | 0.1 | 0.0 |

| | SAMPLE | | | |
|---|---|---|---|---|
| | 1% Methylcellulose | | Distilled Water/ Glycerol/Gelatin | |
| Example No. | $T_1$ (ms) | $T_2$ (ms) | $T_1$ (ms) | $T_2$ (ms) |
| 24 | 1500 | 120 | 722 | 161 |
| 25 | 1590 | 289 | 523 | 214 |
| 26 | 2753 | 213 | 845 | 191 |
| Reference** | 3109 | 484 | 920 | 328 |

*Iron (II, III) oxide black, magnetic pure (Koch Light 3991-00, particle size 10–100 μm)
**Reference values for control with no added contrast agent.

As shown in Table IV below, the effect of the ferromagnetic particles on the spin-lattice relaxation rates ($R_1$ which is equal to $1/T_1$) was moderate, while the spin-spin relaxation rates ($R_2 = 1/T_2$) were increased many times. An interesting observation is the relatively constant value of ratio $R_{2R}/R_{1R}$ ($T_2°T_1/T_2T_1°$ where $T_1°$ and $T_2°$ are the relaxation times in the absence of the contrast agent) in each solution. If the magnetic material is concentrated in few particles, like Type 2, no effect on $R_1$ has been observed while $R_2$ is increased 4 to 5 times. When the magnetic materials are distributed more homogeneously through the sample, as with Type 6, effects on both $R_1$ and $R_2$ are observed.

Fine powdered magnetic materials also show a remarkable effect on $T_2$ while monodisperse polymer particles with manganese ferrite seem to increase both $R_1$ and $R_2$ (Table III above).

Table IV below shows relative relation rates ($R_{1R}$ and $R_{2R}$) and the ratio $R_{2R}/R_{1R}$ in various suspensions of monodisperse ferromagnetic polymer particles. The concentration is 0.1 mmol Fe/kg (5.6 ppm).

TABLE IV

| Example No. | Particle Type | Relative amount of Fe per particle[1] | SAMPLE Water/Glycerol | | |
|---|---|---|---|---|---|
| | | | $R_{1R}$ | $R_{2R}$ | $R_{2R}/R_{1R}$ |
| 27 | 3 | 788 | 1.01 | 4.54 | 4.50 |
| 28 | 9 | 111 | 1.01 | 4.73 | 4.68 |
| 29 | 10 | 61.4 | 1.04 | 4.28 | 4.12 |
| 30 | 4 | 2.6 | 1.65 | 10.39 | 6.30 |
| 31 | 5 | 1.0 | 1.62 | 6.25 | 3.86 |
| 32 | 8 | 0.26 | 2.21 | 11.59 | 5.24 |
| 33 | 7 | 0.26 | 2.63 | 14.29 | 5.43 |
| 34 | 6 | 0.26 | 2.84 | 16.00 | 5.63 |

| Example No. | Particle Type | Relative amount of Fe per particle[1] | SAMPLE Plasma | | |
|---|---|---|---|---|---|
| | | | $R_{1R}$ | $R_{2R}$ | $R_{2R}/R_{1R}$ |
| 27 | 3 | 788 | 1.02 | 2.49 | 2.43 |
| 28 | 19 | 111 | 1.01 | 2.39 | 2.37 |
| 29 | 20 | 61.4 | 1.10 | 3.09 | 2.81 |
| 30 | 4 | 2.6 | 1.88 | 5.58 | 2.97 |
| 31 | 5 | 1.0 | 1.77 | 4.67 | 2.65 |
| 32 | 8 | 0.26 | 2.90 | 6.32 | 2.18 |
| 33 | 7 | 0.26 | 3.33 | 7.81 | 2.35 |
| 34 | 6 | 0.26 | 3.45 | 10.24 | 2.96 |

[1]relative amount of Fe per particle = $d^3x$ where d = particle diameter in $\mu$m x = % Fe in the particle Thus while paramagnetic compounds are particularly effective in reducing the spin-lattice relaxation time ($T_1$), we find ferromagnetic particles to be especially effective in reducing the spin-spin relaxation time ($T_2$).

The observed increase of $R_2$ in the presence of ferromagnetic particles might be explained as follows:

In the $T_2$ relaxation process, no energy is transferred from the nuclei to the lattice. The nuclei in the excited and ground spin states exchange energy with each other, undergoing a spin transition that leaves the net spin state of the whole system unchanged: while one nucleus absorbs energy the cooperating nucleus releases energy.

It is the rate of loss of the transverse magnetization that determines the $T_2$ relaxation time. The transverse magnetization decreases because the nuclear magnetic moments get out of phase. This loss of coherence results from the fact that all nuclear magnetic moments do not have exactly the same precession frequency (due to different local magnetic fields). The decay rate observed ($R_2^*$) is a result to the true spin-spin relaxation rate ($R_2$) together with a contribution which is due to the local inhomogeneity of the magnetic field ($R_{2inh}$).

$$(R_2^*) = (R_2) + (R_{2inh})$$

The observed $T_2^*$ (i.e. $1/R_2$) in a system is always smaller than the real value due to the different magnetic environments of the nuclei. By introducing ferromagnetic material, the local magnetic field inhomogeneities increase resulting in a decrease of the observed $T_2^*$.

In vivo measurements

Various suspensions of monodisperse ferromagnetic polymer particles have been intravenously administered to rats and rabbits and the relaxation times ($T_1$ and $T_2$) in different organs have been measured (post mortem). The obtained relaxation times are summarized in Tables V and VI below. By taking blood samples and measuring relaxation times at various points of time, the elimination of the particles from the vascular system could be followed. The particles were eliminated from the blood extremely rapidly: five minutes after i.v. administration, the particles were substantially eliminated from the vascular system.

As shown in Table VI, the relaxation times ($T_2$) in liver, spleen and lungs were strongly reduced. The relaxation time ($T_2$) in the kidneys was also decreased.

The effects of various amo-nts of the ferromagnetic particles on the relaxation times ($T_1$ and $T_2$) have been studied. It was found that the rate of decrease of the observed relaxation times decreased with increasing concentrations of ferromagnetic particles.

TABLE V

Relaxation times ($T_1$ and $T_2$) in liver (rat) 1 hour after intravenous injection of ferromagnetic particles

| Example No. | Particle Type | mmol Fe/kg bodyweight | $T_1$ ms | $T_2$ ms |
|---|---|---|---|---|
| 35 | 1 | 0.1 | 219 | 22 |
| 36 | 1 | 0.1 | 212 | 23 |
| Reference values** | | | 216 | 39 |

**control - with no contrast agent.

TABLE VI

Relaxation times ($T_1$ and $T_2$) in blood samples and different organs after intravenous injection of ferromagnetic particles.

| Example No. | Injection | Blood | | Bile | |
|---|---|---|---|---|---|
| | | $T_1$ (ms) | $T_2$ (ms) | $T_1$ (ms) | $T_2$ (ms) |
| Control | None | 1024 | 350 3200 | 2500 | — |
| 37 | Particle* Type 3 | 925(5) | 98(5) | 2787 (0-60) | — |
| | 0.5 mmol/kg | 1047(60) | 218(60) | 3632 (60-120) | — |
| 38 | Particle** Type 3 | 878(5) | 149(5) | — | — |
| | 0.5 mmol/kg | 1020(60) | 227(60) | — | — |
| 39 | Particle*** Type 2 0.5 mmol/kg | — | 78(5) | — | — |
| 40 | Particle* Type 2 0.5 mmol/kg | 995(5) | 180(5) | — | — |

| Example No. | Liver/0.9% NaCl (1:2) | | Lung/0.9% NaCl (1:2) | |
|---|---|---|---|---|
| | $T_1$ (ms) | $T_2$ (ms) | $T_1$ (ms) | $T_2$ (ms) |
| Control | 578 | 179 | 1039 | 240 |
| 37 | 369 | 5 | 613 | 11 |
| 38 | 539 | 15 | 687 | 7 |
| 39 | 167 | 3 | 345 | 6 |
| 40 | 284 | 5 | 308 | 6 |

| Example No. | Kidneys/0.9% NaCl (1:2) | | Spleen/0.9% NaCl (1:2) | |
|---|---|---|---|---|
| | $T_1$ (ms) | $T_2$ (ms) | $T_1$ (ms) | $T_2$ (ms) |
| Control | 1224 | 206 | — | — |
| 37 | 768 | 34 | 672 | 6 |
| 38 | 776 | 52 | 379 | 7 |

TABLE VI-continued

Relaxation times ($T_1$ and $T_2$) in blood samples and different organs after intravenous injection of ferromagnetic particles.

| 39 | 645 | 43 | — | — |
| 40 | 672 | 39 | 287 | 4 |

The numbers in the brackets are minutes after the injection
*Killed after 2 hours
**Killed after 90 minutes
***Killed after 30 minutes

TOXICITY

(a) Intravenous administration

Magnetically responding microspheres have been used for biophysical targeting of antitumor agents and other drugs. The toxicity of intravenously administered microspheres has been thoroughly studied. The toxicity of particles has been found to depend on both the size and the shape of the particles.

At present, there rre no published studies describing the toxicity of intravenously administered magnetite. However, intensive human studies have been performed to evaluate the effects of inhaled material. These studies revealed that respiratory intake of moderately large quantities of iron oxides does not cause significant inflammation, fibrosis or alteration of pulmonary function. Based on these results, it may be reasonable to assume that intravascularly administered ferromagnetic compounds will also induce minimal inflamatory responses.

We have studied the acute toxicity of intravenously administered monodisperse ferromagnetic particles. The mortality is summarized in Table VII below while Table VIII below shows the approximate i.v. $LD_{50}$ of various particles in mice.

All injections were performed on male mice, strain NMRI, weighing 18–22 g, obtained from Bomholtgaard, Denmark. Injection site: Tail veins. Injection rate: 0.20 ml/10 sec. Observation period: One week.

The particle solutions were treated by sonication (15 minutes), prior to the injection.

TABLE VII

Toxicity of various ferromagnetic monodisperse polymer particles in mice

| Example No. | Particle Type (and administration mode) | % Fe in particle | Dose in mg particle/ kg bodyweight | Mortality |
|---|---|---|---|---|
| 41 | 4 (i.v.) | 5 | 800 | 0 of 4 |
|  |  |  | 1000 | 0 of 4 |
| 42 | 5 (i.v.) | 2 | 1230 | 0 of 4 |
|  |  |  | 1640 | 0 of 4 |
|  |  |  | 2050 | 0 of 4 |
| 43 | 6 (i.v.) | 0.5 | 600 | 0 of 2 |
|  |  |  | 750 | 0 of 2 |
|  |  |  | 900 | 0 of 2 |
|  |  |  | 1200 | 0 of 2 |
|  |  |  | 1500 | 7 of 7 |
| 44 | 7 (i.v.) | 0.5 | 360 | 3 of 5 |
|  |  |  | 540 | 2 of 5 |
|  |  |  | 720 | 5 of 5 |
|  |  |  | 810 | 5 of 5 |
|  |  |  | 900 | 5 of 5 |
| 45 | 2 (i.v.) | 30.2 | 500 | 0 of 5 |
|  |  |  | 750 | 1 of 5 |
|  |  |  | 1000 | 2 of 2 |
|  |  |  | 1250 | 2 of 2 |
| 46 | 3 (i.v.) | 29.2 | 750 | 0 of 2 |
|  |  |  | 1250 | 0 of 4 |
|  |  |  | 1500 | 0 of 4 |
|  |  |  | 2000 | 4 of 4 |
|  |  |  | 2250 | 3 of 4 |
|  |  |  | 3000 | 2 of 2 |
| 47 | 3 (oral) | 29.2 | 7810 | 0 of 5 |

TABLE VIII

| Example No. | Particle Type | Particle diameter μm | % Fe in particle | Approximate $LD_{50}$ mg particles/kg bodyweight |
|---|---|---|---|---|
| 48 | 4 | 0.8 | 5 | >1000 |
| 49 | 5 | 0.8 | 2 | >2050 |
| 50 | 6 | 0.8 | 0.5 | 1350 |
| 51 | 7 | 0.8 | 0.5 | 450 |
| 52 | 2 | 1.5 | 30.2 | 750–1000 |
| 53 | 3 | 3.0 | 29.2 | 1500–2000 |

| Example No. | Approximate $LD_{50}$ mg Fe/kg bodyweight | Approximate $LD_{50}$/ED |
|---|---|---|
| 48 | >50 | >360 |
| 49 | >41 | >290 |
| 50 | 6.8 | 49 |
| 51 | 2.3 | 16 |
| 52 | 230–300 | 1700–2100 |
| 53 | 440–580 | 3100–4100 |

The especially low $LD_{50}$ values with particle Type 2 as compared with Type 3 and with Type 7 as compared with Types 4, 5 and 6 may be due to flocculation of the particles.

If all the particles were picked up by the reticuloendothelial cells in the liver, about 0.14 mg Fe/kg bodyweight could be enough to give a contrast enhancement. (0.1 mmol Fe/kg liver, and the liver constitutes about 2.6% of the bodyweight). As shown in Table VIII, the estimated "safety factor" (approximate $LD_{50}$/effective dose (ED)) is large.

(b) Oral administration

The toxic properties of orally administered particulate ferromagnetic substances as magnetite and ferrites have been described. No changes in any of the biochemical and physiological parameters were observed when a single dosis of 2.0 g/kg bodyweight or 20 g/kg as repeated doses were given rats and mice.

We have studied the toxicity of orally administered monodisperse ferrogmagnetic particles (Type 3). No sign of toxic effect was observed after 7.8 g particles/kg bodyweight.

During the first 24 hours 92.4% of the dose were recovered in the faeces.

The material is insoluble in water and thereby is not absorbed from the gastrointestinal tract. (The polymer matrix for Type 3 particles is not biodegradable).

The invention is also illustrated by the following further non-limiting Examples:

TABLE IX (In vitro test results)

| Example No. | Particle type | Particle diameter (μm) | Amount of Fe in particle (%) |
|---|---|---|---|

TABLE IX-continued (In vitro test results)

| | | | |
|---|---|---|---|
| 54 | 17[1] | 3.0 | 0.52 |
| 55 | 18[2] | 0.3–4.0 | 10.0 |
| 56 | 19[3] | 0.3–4.0 | 8.6 |
| 57 | 20[4] | 0.6 | 69.9 |
| 58 | 21[5] | 0.3–0.6 | 69.9 |
| 59 | 22[6] | 0.5–2.0 | 44.0 |
| 60 | 23[7] | 0.01–0.02 | 72.4 |

| Example No. | Concentration of Fe in sample* (mmol/kg) | $T_1$ (ms) | $T_2$ (ms) |
|---|---|---|---|
| 54 | 0.25 | 291 | 48 |
| 55 | 0.25 | 1236 | 59 |
| 56 | 0.25 | 107 | 10 |
| 57 | 0.25 | 1356 | 182 |
| 58 | 0.25 | 1225 | 124 |
| 59 | 0.25 | 363 | 24 |
| 60 | 0.25 | 723 | 27 |
| Control | | 1332 | 445 |

[1] Monodisperse particles prepared according to the process of J. Ugelstad et al. (WO 83/03920). Density 1.07 g cm$^{-3}$.
[2] Estrapor ® LMP 233 from Rhône-Poulenc, Paris, France.
[3] Estrapor ® LMC 247 from Rhône-Poulenc, Paris, France.
[4] γ-Fe$_2$O$_3$ (Bayferrox 8060 from Bayer AG, Leverkusen, W-Germany)
[5] Black Iron Oxide (11557 from D. F. Anstead Ltd. Billericay, Essex, England)
[6] Biomag M4200 (Advanced Magnetics Inc., Cambridge, Massachusetts, U.S.A.)
[7] Ferrofluid (Ferrofluid Co., U.S.A.)
*Distillied and ion-exchanged water 77.3 weight %
Glycerol 13.6 weight %
Gelatin 9.1 weight %

EXAMPLE 61

(Preparation of a suspension for oral administration)

| | |
|---|---|
| Particles (Type 9) | 3.04 g |
| Sodium polymetaphosphate | 18.25 g |
| Saccharin sodium | 1.0 g |
| Methyl parahydroxybenzoate | 0.75 g |
| Potassium sorbate | 1.0 g |
| Xanthan gum | 3.0 g |
| Peppermint oil | 2.0 g |
| Water | 971.0 g |

Methyl parahydroxybenzoate was dissolved in hot water (90° C.). The solution was cooled and xanthan gum was added, and the mixture was vigorously stirred for 1 h. Sodium polymetaphosphate, saccharin sodium, potassium sorbate and peppermint oil were dissolved, and finally the particles were suspended. The suspension was filled in a 1 liter bottle. The suspension contained 1.0 mg Fe/g.

EXAMPLE 62

(Preparation of a of a suspension for oral use)

| | |
|---|---|
| Magnesium aluminium silicate (e.g. Veegum) | 5.0 g |
| Liquid sorbitol 70% | 478.0 g |
| Citric acid | 1.0 g |
| Methyl parahydroxybenzoate | 0.8 g |
| Orange essence | 0.2 g |
| Ethanol | 15.0 g |
| Particles (Type 21) | 1.32 g |
| Water | 498.6 g |

Veegum was dispersed in water at 60° C. by high speed mixing for 1 hour. Liquid sorbitol and citric acid were added under continuous stirring. A solution of methyl parahydroxybenzoate and orange essence in ethanol was added and the particles were suspended under vigorous stirring. The suspension was filled in a 1 liter bottle. The suspension contained 1 mg Fe/g.

EXAMPLE 63

(Preparation of a suspension for oral administration)

| | |
|---|---|
| Particles (Type 8) | 10 g |
| Hydroxyethyl cellulose | 10.0 g |
| Methyl parahydroxybenzoate | 0.8 g |
| Propyl parahydroxybenzoate | 0.2 g |
| Ethanol | 10.0 g |
| Saccharin sodium | 1.0 g |
| Orange essence | 0.3 g |
| Apricot essence | 0.7 g |
| Water | 967.0 g |

Hydroxyethyl cellulose was dispersed in water with stirring for 2 hours. Saccharin sodium and a solution of the essences, methyl and propyl parahydroxybenzoate in ethanol were slowly added. The particles were dispersed in the solution under vigorous stirring. The suspension contained 0.05 mg Fe/g.

EXAMPLE 64

(Preparation of a suspension for rectal administration (enema))

Methyl parahydroxybenzoate (85 mg) and propyl parahydroxybenzoate (15 mg) were dissolved in water (100 ml) at 90° C. After cooling to 30° C. methyl cellulose (2g) was added and the mixture was agitated for 2 hours. 1.0 g of particles (Type 5) was suspended. The suspension was filled in a 100 ml tube. The suspension contained 0.2 mg Fe/ml.

EXAMPLE 65

(Preparation of a suspension for use in sialography/nmr-examination of the urine bladder and/or hysterosalpingography)

| | |
|---|---|
| Particles (Type 17) | 1.0 g |
| Polyoxyethylene polyoxypropylene copolymer (e.g. Pluronic F68) | 0.5 g |
| Sodium chloride | 0.9 g |
| Sterile water | ad 100 ml |

The particle were aseptically suspended in a sterile mixture of sodium chloride and Pluronic in water. The suspension was filled into single dose containers. The suspension contained 52 mg Fe/l.

EXAMPLE 66

(Preparation of suspension of coated particles for administtration)

| Solution A | |
|---|---|
| Methacrylate esters copolymers (e.g. Eudragit RS) | 50 g |
| Talcum | 50 g |
| Isopropanol | 900 g |

Talcum was suspended in a solution of Eudragit RS in isopropanol under stirring.

100 g of the solution A were sprayed upon 500 g of magnetite particles (Example 26). The particles were rotated in a fluidised bed apparatus. The amounts and the temperature of the inlet air were adjusted so that the particles were kept at a temperature of 30° C. and were sprayed continuously. The spraying was carried on until sufficient coating was obtained. The particles were dried overnight at ambient temperature and filled into single dose containers.

| Solution B. | |
|---|---|
| Cellulose gum | 1.0 g |
| Sodium chloride | 0.5 g |
| Methyl parahydroxybenzoate | 0.1 g |
| Ethanol | 2.0 g |
| Peppermint oil | 0.5 g |
| Water | 96.0 g |

The cellulose gum, sodium chloride and peppermint oil and methyl parahydroxybenzoate in ethanol were dissolved in water.

Preparation of the final suspension 130 ml of solution B were added to 2.8 g of the coated particles and the container was shaken until homogenous suspension. The suspension contained 20 mg Fe/ml.

EXAMPLE 67

(Preparation of enterosolubly coated particles for oral use)

This suspension was prepared as described in Example 66. Eudragit S was used instead of Eudragit RS. The pH in the suspending solution (Solution B) was adjusted to 4 with 1N HCl.

We claim:

1. In a method of NMR imaging of a sample which comprises introducing a contrast agent into the sample and generating an image of the sample, wherein the improvement comprises introducing into the sample a contrast agent comprising a plurality of particles of a ferromagnetic material of about 0.6 micrometer or less in size and generating as the image of the sample a $T_2$-dependent image.

2. A method as claimed in claim 1 of nmr imaging of a human or non-human animal body to produce an nmr image suitable for use in diagnosis wherein said contrast agent is introduced into the region of said body of which said image is generated.

3. A method as claimed in claim 2 wherein said contrast agent is administered to said body parenterally.

4. A method as claimed in claim 3 wherein said image is an image of tissue for which said contrast agent is tissue-specific.

5. A method as claimed in claim 4 wherein said image is of the liver or spleen.

6. A method as claimed in claim 2 wherein said contrast agent is in the form of a dispersion of particles in a physiologically acceptable dispersion medium.

7. A method as claimed in claim 6 wherein said contrast agent is introduced into the bladder, uterus, biliary duct or parotid duct or into the digestive tract of said body.

8. A method as claimed in claim 7 wherein said particles of ferromagnetic material are embedded in or coated with a non-ferromagnetic matrix or coating of a non-biodegradable, biotolerable polymer.

9. A method as claimed in claim 8 wherein said coated or matrix-embedded particles have a maximum dimension in the range 0.1 to 20 μm and have a ferromagnetic content of from 0.5 to 50% by weight.

10. A method as claimed in claim 9 wherein said coated or matrix-embedded particles have a maximum dimension in the range of from 5 to 20 um.

11. A method as claimed in claim 7 wherein said contrast agent comprises a viscosity enhancing agent and/or a surfactant.

12. A method as claimed in claim 1 wherein said $T_2$ dependent image is $T_2$ image.

13. A method as claimed in claim 12 wherein said image is a spin-echo image.

14. A method as claimed in claim 1 wherein said contrast agent comprises particles of at least 0.002 micrometer in size.

15. A method as claimed in claim 1 wherein said contrast agent comprises particles of at least 0.002 micrometer in size.

16. A method as claimed in claim 1 wherein said contrast agent comprises uncoated particles of a ferromagnetic material.

17. A method as claimed in claim 1 wherein said ferromagnetic material is a magnetic iron oxide.

18. A method as claimed in claim 17 wherein said ferromagnetic material is a ferrite.

19. A method as claimed in claim 17 wherein said ferromagnetic material is magnetite or $\gamma$-$Fe_2O_3$.

20. In a method of NMR imaging of a sample which comprises introducing a contrast agent into the sample and generating an image of the sample, wherein the improvement comprises introducing into the sample a contrast agent comprising a plurality of ferrite particles of about 0.6 micrometer or less in size and generating as the image of the sample a $T_2$-dependent image.

21. A method as claimed in claim 20 wherein said ferrite particles are of about 0.02 micrometer or less in size.

22. A method as claimed in claim 21 wherein said ferrite particles are uncoated or are embedded in a non-ferromagnetic matrix.

23. A method as claimed in claim 20 wherein said ferrite particles are uncoated or are embedded in a non-ferromagnetic matrix.

24. A method as claimed in claim 20 wherein said image is a spin-echo image.

25. In a method of NMR imaging of a sample which comprises introducing a contrast agent into said sample and generating an imaging of said sample, wherein the improvement comprises introducing into said sample a contrast agent comprising a plurality of superparamagnetic particles and generating as said image of said sample a $T_2$-dependent image.

26. A method as claimed in claim 25 of NMR imaging of a human or a non-human animal body to produce an NMR image suitable for use in diagnosis wherein said contrast agent is introduced into the region of said body of which said image is generated.

27. A method as claimed in claim 26 wherein said contrast agent is in the form of a dispersion of particles in a physiologically acceptable dispersion medium.

28. A method as claimed in claim 27 wherein said contrast agent is introduced into the bladder, uterus, biliary duct or parotid duct or into the digestive tract of said body.

29. A method as claimed in claim 28 wherein said superparamagnetic particles are embedded in or coated with a non-ferromagnetic matrix or coating of a non-biodegradeable, biotorable polymer.

30. A method as claimed in claim 29 wherein said coated or matrix-embedded particles have a maximum dimension in the range 0.1 to 20 micrometers.

31. A method as claimed in claim 28 wherein said contrast agent comprises a viscosity enhancing agent and/or a surfactant.

32. A method as claimed in claim 25 wherein said image is a $T_2$-dependent image.

33. A method as claimed in claim 32 wherein said $T_2$ dependent image is a $T_2$ image.

34. A method as claimed in claim 33 wherein said image is a spin-echo image.

35. In a method of NMR imaging of a sample which comprises introducing a contrast agent into said sample and generating an image of the sample, wherein the improvement comprises introducing into said sample a contrast agent comprising a plurality of particles of a biotolerable polymeric matrix carrying particles of a ferromagnetic material of about 0.6 micrometer or less in size and generating as said image of said sample a $T_2$-dependent image.

36. In a method of NMR imaging of a sample which comprises introducing a contrast agent into said sample and generating an image of said sample, wherein the comprises introducing into said sample a contrast agent comprising a plurality of particles of a biotolerable polymeric matrix carrying superparamagnetic particles and generating as said image of said sample a $T_2$-dependent image.

* * * * *

UNITED STATES PATENT AND TRADEMARK OFFICE
CERTIFICATE OF CORRECTION

PATENT NO. : 4,863,715

DATED : September 5, 1989

INVENTOR(S) : Trond Jacobsen et al

It is certified that error appears in the above-identified patent and that said Letters Patent is hereby corrected as shown below:

Claim 10, line 3, delete "um" and insert —µm—.

Claim 14, line 2, delete "at least 0.002" and insert —about 0.02—.

Claim 29, line 4, delete "biotorable" and insert —biotolerable—.

Claim 36, line 4, please insert —improvement— at the beginning of the line.

Signed and Sealed this

Sixteenth Day of October, 1990

Attest:

HARRY F. MANBECK, JR.

*Attesting Officer*      *Commissioner of Patents and Trademarks*